(12) United States Patent
Cornil et al.

(10) Patent No.: US 8,246,667 B2
(45) Date of Patent: Aug. 21, 2012

(54) EQUIPMENT FOR TREATING WOUNDS AND METHOD FOR THE BIOCHEMICAL ACTIVATION OF HEALING

(75) Inventors: Alain Cornil, Aix En Provence (FR); Alexandre Capon, Verlinghem (FR); Alban Gosse, Mimet (FR); Patrick Peronne, Aix En Provence (FR)

(73) Assignee: EKKYO, Aix-en-Provence (FR)

( * ) Notice: Subject to any disclaimer, the term of this patent is extended or adjusted under 35 U.S.C. 154(b) by 592 days.

(21) Appl. No.: 12/522,970

(22) PCT Filed: Jan. 29, 2008

(86) PCT No.: PCT/FR2008/000102
§ 371 (c)(1),
(2), (4) Date: Jul. 13, 2009

(87) PCT Pub. No.: WO2008/107563
PCT Pub. Date: Sep. 12, 2008

(65) Prior Publication Data
US 2010/0063489 A1    Mar. 11, 2010

(30) Foreign Application Priority Data
Jan. 29, 2007  (FR) .................................... 07 52934

(51) Int. Cl.
*A61N 5/06* (2006.01)
(52) U.S. Cl. .................. 607/89; 606/8; 606/9
(58) Field of Classification Search ............ 607/89; 606/8, 9
See application file for complete search history.

(56) References Cited

U.S. PATENT DOCUMENTS

| | | | |
|---|---|---|---|
| 5,156,613 | A | 10/1992 | Sawyer |
| 6,773,699 | B1 | 8/2004 | Soltz et al. |
| 2002/0111609 | A1* | 8/2002 | Mordon et al. .................. 606/8 |
| 2006/0089629 | A1 | 4/2006 | Howe et al. |
| 2009/0062718 | A1* | 3/2009 | Cornil .............................. 604/20 |

FOREIGN PATENT DOCUMENTS

| | | |
|---|---|---|
| EP | 0976362 | 2/2000 |
| WO | WO-9717025 | 5/1997 |
| WO | WO-2004010885 | 2/2004 |
| WO | WO-2007080239 | 7/2007 |
| WO | WO-2007138217 | 12/2007 |

OTHER PUBLICATIONS

European Patent Office, International Search Report, dated Sep. 11, 2008 (4 pgs English language, 4 pgs French language).

* cited by examiner

*Primary Examiner* — Kinam Park (57) ABSTRACT

This invention concerns a system for dermatological treatment including an energy source suitable for biochemically activating healing and including at least one means of interaction between the energy source and the patient. The means of interaction is composed of a continuous adhesive support suitable for placement close to the area to be treated, the support having a means of identification and interacting without contact with a sensor allowing the energy source to function only when the distance between the sensor and the means of identification is less than a threshold value. The invention also concerns such a continuous adhesive support and a method of dermatological treatment.

21 Claims, 6 Drawing Sheets

EQUIPMENT FOR TREATING WOUNDS AND METHOD FOR THE BIOCHEMICAL ACTIVATION OF HEALING

CROSS REFERENCE TO RELATED APPLICATIONS

This application is a National Stage filing under 35 U.S.C. §371 of PCT Application No. PCT/FR208/000102, filed Jan. 29, 2008. This application also claims the benefit of French Application No. 0752934, filed Jan. 29, 2007. The entirety of both applications is incorporated herein by reference.

FIELD OF INVENTION

This invention concerns the treatment of wounds using a laser beam, and the equipment for such treatment.

BACKGROUND OF INVENTION

In the current state of the art we know of patent FR9809557 which concerns a method and a device for assisting wound closure which combines a laser with a transparent adhesive dressing. The dressing is intended to bring together the edges of a cutaneous incision while the laser is used to heat these very tissues through the dressing and thus contribute to healing. However, this quick and simple-to-use system suffers from several faults.

During its clinical use in humans, it was found that the incisions produced exudates which spread between the dressing and the skin thus destroying adhesion of the dressing in the area around the incision. However, to obtain satisfactory results it is essential that the edges of the wound are kept in close contact throughout the period up to complete closure of the wound. If this is not the case, greater fibrosis occurs in the open space resulting in the appearance of scar tissue and an increased risk of infection.

Given the length and curved shape of some surgical wounds, it is very difficult to apply a single dressing uniformly to them. To guarantee good approximation of wounds, multiple strips of dressing placed side by side need to be used, thus increasing the risk of post-operative infection.

There is therefore an advantage in proposing a method of wound closure which does not present an obstacle to the flow of exudates while producing good approximation of the edges. The use of sutures or staples would seem to provide an answer to this problem. However the material used must have a source energy absorption coefficient lower than or equal to that of the skin in which it is implanted in order to avoid it getting too hot.

Another limitation of the patent concerns the safety measures for the laser used. Two other patents currently being submitted (submissions FR0600160 and FR0651942) describe devices and methods for making triggering the laser safe by allowing its activation only when the dressing is detected by that laser.

Generally speaking, lasers used for dermatological applications have no system for automatically detecting the area to be treated. The device we describe here provides this feature and thus makes the functioning of this type of laser safe while not obstructing the area treated.

SUMMARY OF THE INVENTION

The device proposed according to the invention is comprised of an energy source for activating a biochemical effect in the skin. The energy source is associated with an identification device with or without contact placed close to the area to be treated but not covering it.

The energy source can only be activated when the sensor associated with it detects the identification device.

To be able to be used for wound closure, the device is combined with a mechanical support element inserted within the thickness of the skin allowing the edges of the wound treated to be held together, the material and dimensions of which are chosen so as to avoid causing excessive heating or burning of the tissues treated by the energy source.

Using the invention, we can maintain good approximation of wounds throughout the period of healing while keeping the laser safe and setting its parameters according to the type of incision and the tissue being treated.

More precisely, the invention concerns a system for dermatological treatment comprising an energy source suitable for the biochemical activation of healing and at least one means of interaction between the energy source and the patient, characterized in that the said means of interaction is composed of a continuous adhesive support suitable for placing close to the area to be treated, the said support having a means of identification interacting without contact with a sensor that allows the energy source to function only when the distance between the sensor and the said means of identification is below a threshold value.

According to particular embodiments:
The adhesive support contains at least 2 means of identification spaced at a distance at least equal to a whole multiple of the width of the area treated by an individual shot;
The means of identification are spaced at a distance equal to the width of the area treated by an individual shot;
The means of identification interacts with the energy source through a contact;
The functioning parameters of the energy source are memorized in the means of identification and communicated to the device controlling the energy source;
Information on the state of the area under treatment is provided by an adhesive support fitted with a means of identification placed near the area to be treated and recording this information in the means of identification. The information relates to one of the following states:
The area to be treated has not been treated,
The area to be treated is being treated,
Treatment of the area to be treated has been completed;
The control device which receives the information concerning the state of the area under treatment includes means of preventing second use of the adhesive support containing a means of identification when the support has already been used once for treatment of an area to be treated;
The system for dermatological treatment is combined with a wound closure device placed in the edges of the wound which has an absorption coefficient for the energy source under consideration lower than that of the skin;
The system for dermatological treatment consists of a handpiece incorporating a source of electromagnetic radiation for biochemically activating healing and a means of interacting with the said adhesive support;
The system for dermatological treatment consists of a handpiece incorporating a laser source and a means of interacting with the said adhesive support;
The system for dermatological treatment includes a source of energy controlled by a microprocessor receiving a signal from a sensor able to interact with the means of identification of the dressing or adhesive support;

The handpiece includes a radiofrequency reader; and

The range of the radio-frequency antenna is less than 5 mm.

The invention also concerns an adhesive support for a system for the dermatological treatment set out above which includes a means of preventing second use of the adhesive support if it has already been used for the treatment of an area to be treated.

According to particular embodiments:

The adhesive support includes a transponder;

The transponder of the adhesive support functions in a frequency band between 13 and 14 MHz;

On its upper surface the adhesive support has markings spaced apart by a distance equal to the width of the area treated by an individual shot; and The adhesive support is opaque.

The invention also concerns a method of dermatological treatment suitable for biochemical activation of healing in a patient comprised of the following stages:

(i) positioning, near the area to be treated, of an adhesive support which has a means of identification which interacts without contact with a sensor controlling functioning of an energy source; and (ii) positioning of the said energy source, including a sensor controlling its functioning, at a distance between the said sensor and the said means of identification that is less than a threshold value so that the said source of energy is activated and biochemical activation of healing occurs in the area under treatment.

According to a preferred embodiment, the method of dermatological treatment is suited to the closure of wounds.

In a particular embodiment, the method of dermatological treatment includes a preliminary step where a wound closure device is inserted into the edges of the wound. This device has an absorption coefficient for the energy source under consideration lower than that of the skin.

In a preferred embodiment, the wound closure device consists of an adhesive support fitted with an RFID tag composed of an electronic memory with an antenna, a laser handpiece with an RFID detection system and a continuous suture thread inserted in the thickness of the wound and throughout its length.

The RFID tag, ideally compatible with the standard ISO 15693, consists of a conventional electronic chip, e.g. NXP i-code SLI or SLI-S, Inside Contactless Picopass 2k or ST LRI 2K. The tags and the handpiece RFID reader use a frequency band between 10 and 20 MHz, preferably a frequency band between 13 and 14 MHz, thus allowing readings to be made at short distances. To advantage, the antenna of the tags and RFID reader are specially designed to make the device safe and to stop firing once the tag leaves the reading field (a distance of more than 10 mm).

To advantage, the said adhesive support may be in several lengths (e.g. 4, 10 and 20 cm) and may also be in the form of a roll used to obtain an adhesive support of the desired length.

BRIEF DESCRIPTION OF THE DRAWINGS

The invention will be better understood by reading the following description and referring to the figures attached, namely.

DETAILED DESCRIPTION OF THE INVENTION

Figure 1:
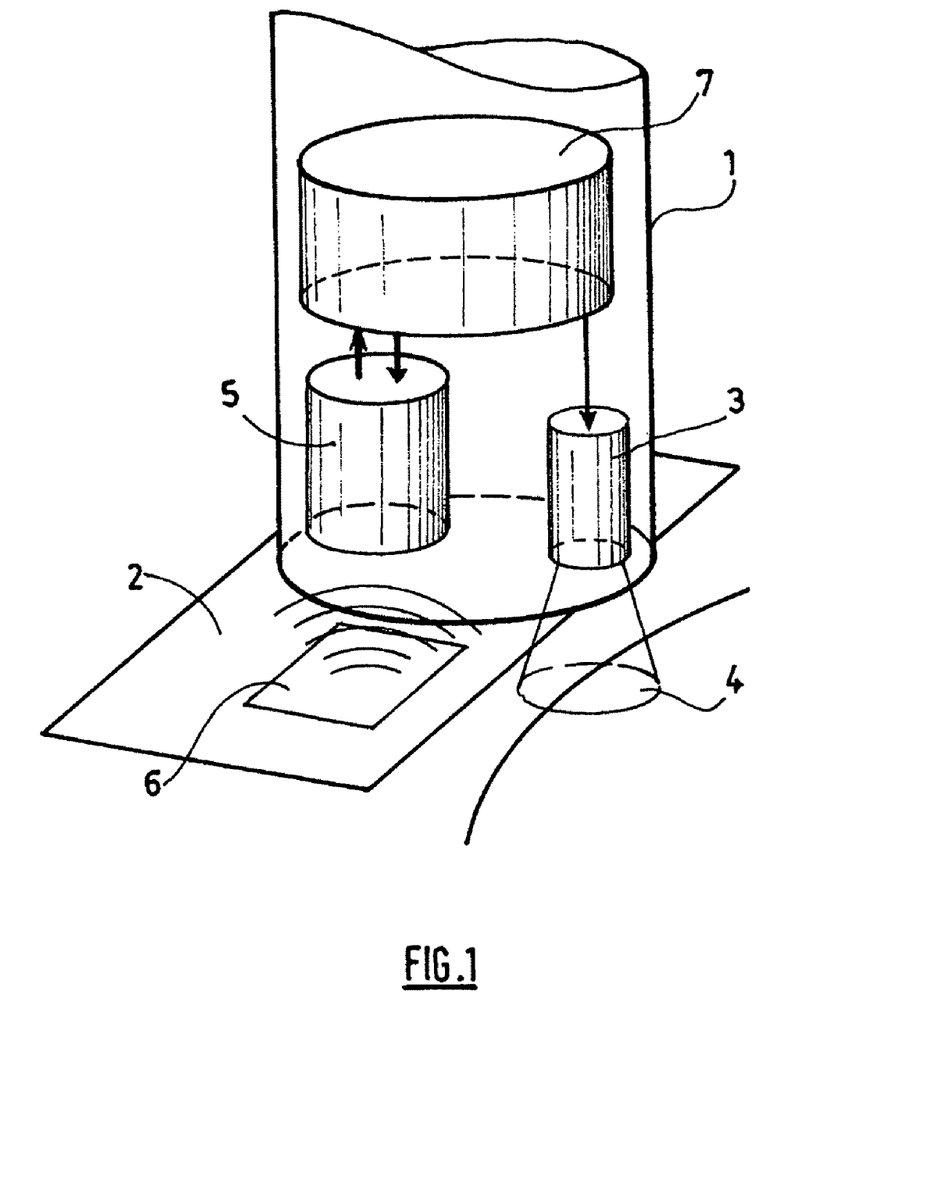
FIG. 1 is a diagram of the principle of the system according to one variant.

With reference to FIG. 1, the device is composed of two main parts: a handpiece (1); and an adhesive support (2).

The handpiece (1) includes a source of excitation able to provoke a biochemical effect on the wound. In the example described this is a laser source (3) producing a spot (4) when it is projected onto the surface of the patient's skin.

The handpiece (1) also contains a reader (5) interacting with a marker (6) contained in the support (2).

The handpiece (1) also includes an electronic control circuit (7). This circuit conditionally controls the functioning of the laser (3), particularly its activation when the handpiece is situated near the skin of the patient and the area to be treated, as well as the power of the laser.

The proximity of the area to be treated is detected by analysis of signals from the reader (5) depending on exchanges with the marker (6).

The firing parameters of the laser are controlled as a function of the nature of the information transmitted by the marker (6), which contains parameters which can modify the power, duration and number of shots according to the user's wishes. The user selects the support depending on the nature of the treatment to be performed, and the support selected sends the receiver (5) a signal or item of information which controls firing of the laser (3). Several variants of the adhesive support are available depending for example on:

the indication for use;

the patient's skin type (phototype, thickness, age, location).

They allow the user to meet his needs directly without having to worry about the parameters to be used for the treatment.

The support (2) consists for example of a patch comprised of a piece of adhesive fabric including a radiofrequency identification device (RFID) constructed with an antenna design allowing inductive coupling supplying an HF component and transmission of the high frequency signal from this component.

The support is positioned near the zone to be treated so that the handpiece is within range of interaction with the RFID for the period of treatment.

The distance between the support and the handpiece is between one and fifteen centimeters. The distance is assessed by a limited range of the means of interaction between the support and the handpiece, or by using a range-finder, for example an ultrasound range-finder, incorporated into the handpiece.

The system also includes a suture thread. This thread is so placed as to approximate the edges of the wound perfectly. The material of this thread is chosen to have an optical absorption coefficient at the wavelength of the laser which is not greater than that of cutaneous tissue, e.g. a PGLA (polyglycolic/lactic acid) copolymer.

The adhesive support is placed immediately next to the wound so that the detector of the laser handpiece is within detection range of the support and so that the laser beam is perpendicular to the area to be treated. This proximity ensures that the device is safe by preventing firing immediately if the tag within the adhesive support becomes out of range of the reader in the handpiece. The range is therefore a maximum of 10 mm. At a greater distance, the adhesive support can no longer play its role of locking the device and making it safe. The distance of the adhesive support from the incision to be treated is also important. It must be placed longitudinally close to the incision, ideally less than 10 mm away, so as to avoid interfering with treatment of the incision by the device and so as not to cause involuntary pulling on the incision which could adversely affect approximation of the edges of the wound.

When long wounds are to be treated, the adhesive strip has several tags equally spaced at whole multiples of the width of the treatment beam, in order to control the spacing of shots, the effective firing time and the total energy delivered.

The adhesive support has a triple role:

It makes the device safe: the device immediately ceases to function as soon as the tag in the adhesive support is out of range of the REID reader contained in the handpiece;

It defines the treatment parameters: the user selects the adhesive support depending on the indication and the patient's skin type, and the pre-programmed tags in the adhesive support directly send the appropriate parameters to the device; and It maintains its single use feature intact: during use, the device records information in the tags contained in the adhesive support concerning treatment status. The treatment statuses are as follows:

The area to be treated has not been treated.

The area to be treated is being treated, and treatment of the area to be treated has been completed.

The control device receiving the information about the state of the area to be treated includes means of preventing second use of the adhesive support containing a means of identification once the treatment has been completed, when it has already been used once for treatment of an area to be treated. This tag-locking principle thus ensures that each adhesive support is only used once. The direct advantage of this system is that it is impossible to:

apply a treatment twice in the same place (elimination of the risk of overdose); and re-use an adhesive support, sterile on delivery, which has already been used.

The means of preventing second use of the adhesive support could be directly included in the means of identification itself.

With the further aim of helping the user ensure that the surgical or medical procedure runs smoothly, the adhesive supports have a fourth function of assisting and monitoring the procedure.

Figure 2:
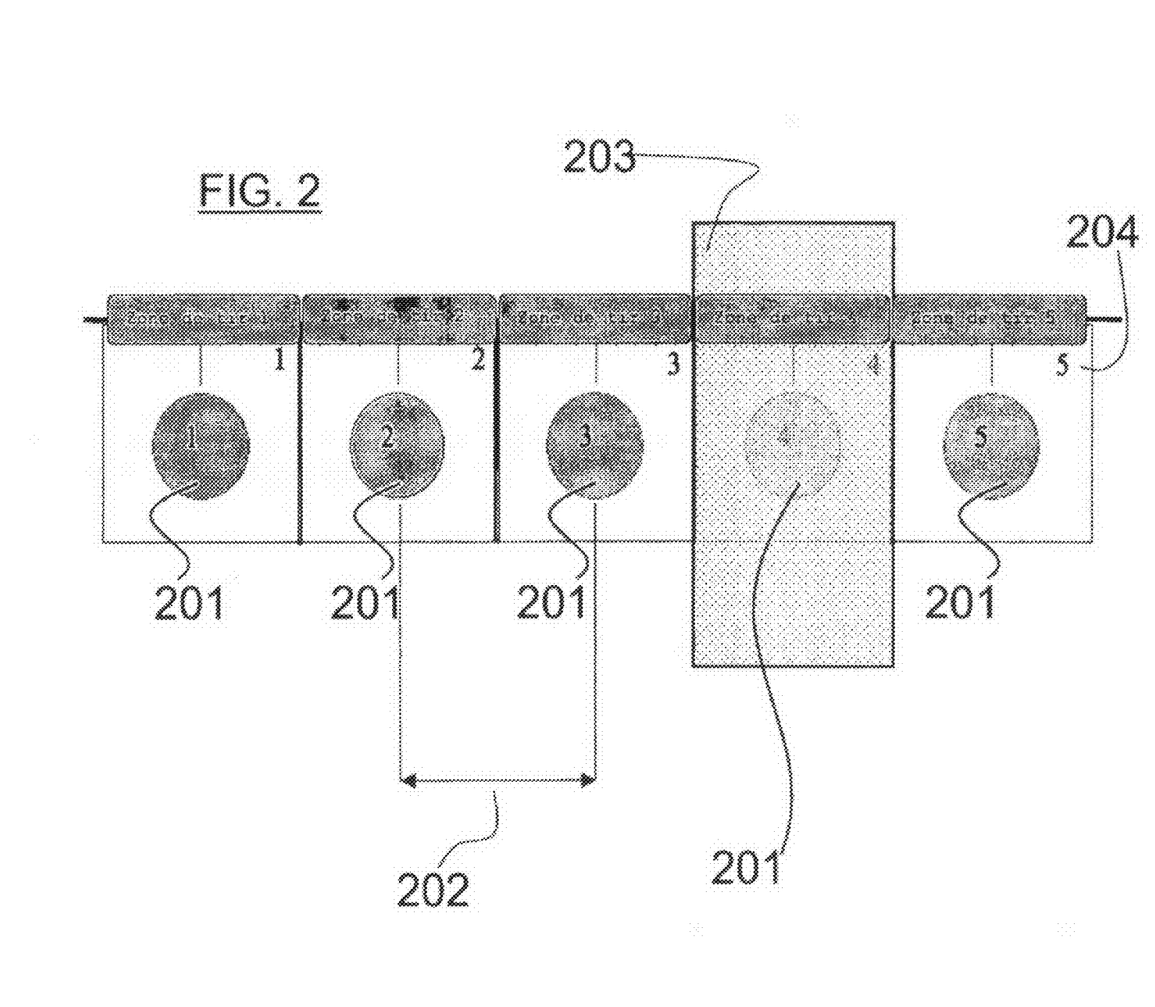
FIG. 2 is a schematic view of the adhesive support.

The adhesive support actually has a guide system allowing the user to monitor treatment, for example, throughout the length of an incision (FIG. 2). This guide system works through specific numbering of the tags, a rule or a system of graduation. This visual system allows the user firstly to monitor the treatment, and secondly to have a mnemotechnical means of knowing the place where he stopped if the treatment is interrupted involuntarily.

With reference to FIG. 2, in the case of treatment of an area requiring several contiguous shots, the adhesive support contains several tags (201) spaced at a distance equivalent to the width of the beam fired (202). In this way, the tag not only controls activation of the laser but also its positioning (203) in the event of contiguous shots and the effective firing time and consequently the dose of energy delivered with each shot.

The adhesive support has visual markers (204) allowing the laser to be precisely positioned over the tag.

Figure 3:
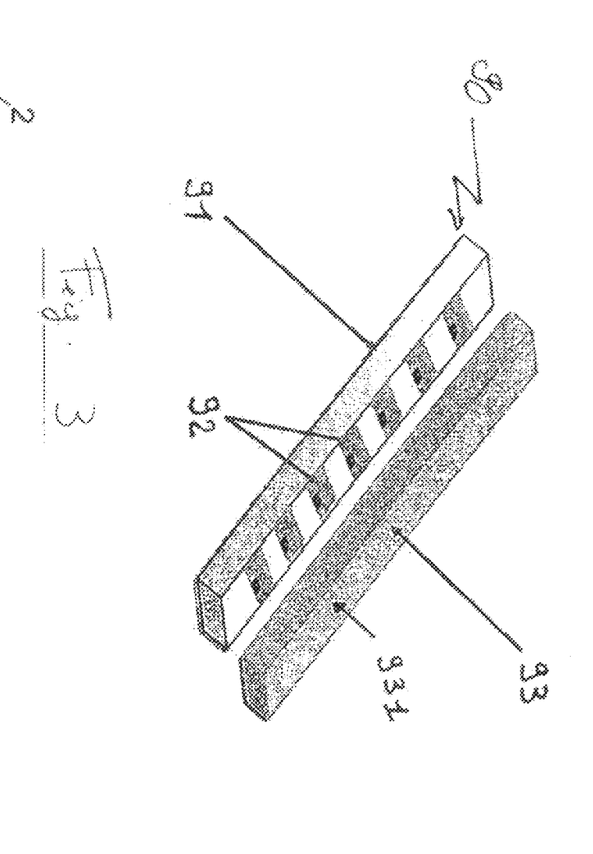
FIG. 3 is a view of the adhesive support in perspective communicating with the handpiece.

With reference to FIG. 3, it is intended to make the treatment safe and set its parameters using an adhesive support (90) containing an RFID chip which will communicate the various functioning parameters to the handpiece depending on the indication for use and the phototype of the patient to be treated. This adhesive support (90), which may be available in several lengths (e.g. 4, 10 and 20 cm), is stuck on approximately 5 mm from the area to be treated.

The adhesive support (90) is composed of two adhesive sub-supports: one sub-support (91) adhesive on both sides and another sub-support adhesive (93) on one side. The RFID tags (92) which will be positioned every 2 cm are sandwiched between these two sub-supports. The adhesive support (90) may for example be 2 cm wide.

The lower adhesive sub-support (91) is in contact with the patient's skin Consequently, it must comply with biocompatibility issues and retain sufficient hold on the skin during use. The lower adhesive sub-support (91) must be able to stick to the skin of the patient and be assembled both with the RFID tag and the upper adhesive sub-support (93). Consequently, the lower adhesive sub-support is adhesive on both sides.

Manufacture of the adhesive supports (90) includes a sterilization stage.

Figure 4:
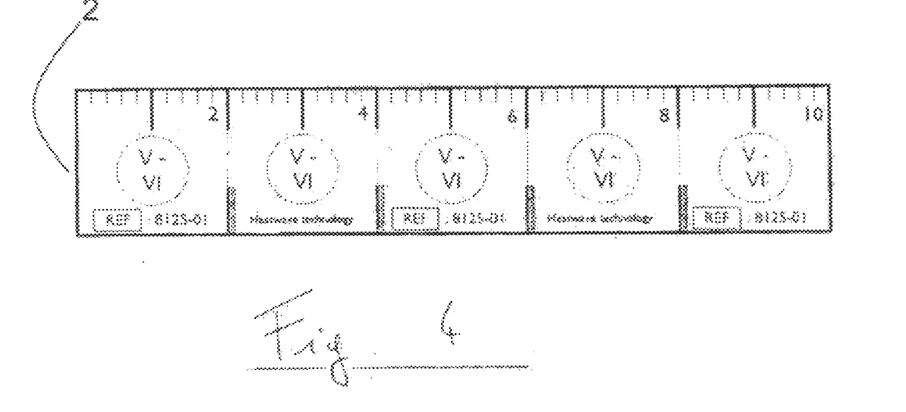
FIG. 4 is a view of the adhesive support.

The upper adhesive sub-support (93) must be adhesive on one side only so that it can be assembled with the RFID tags (92) and the lower adhesive sub-support (91). With reference to FIG. 4, on its upper part (93) information may be printed such as the phototype, the name of the company, a graduation system, to allow the practitioner to know where he is as far as the treatment is concerned as well as the product reference.

The upper adhesive sub-support (93) is such that it does not distort RFID communication between the RFID reader of the handpiece and the RFID tags (92).

The RFID tags (92) comply with the standard ISO 15693. Moreover, the intention is to implement the compulsory and optional parts set out in this standard. As the distance of the reader from the RFID tag is a critical aspect, the RFID tags (92) according to the invention are such that they allow this value to be fixed once the "RFID tag-RFID reader" pair has been selected. For example, the dimensions of the RFID tags may be 14 mm×14 mm and be less than 1 mm thick. It is intended that the storage capacity of the RFID tag EEPROM should be a minimum of 1024 bytes. In addition, it is intended to use an ethylene oxide sterilization procedure.

Figure 5:
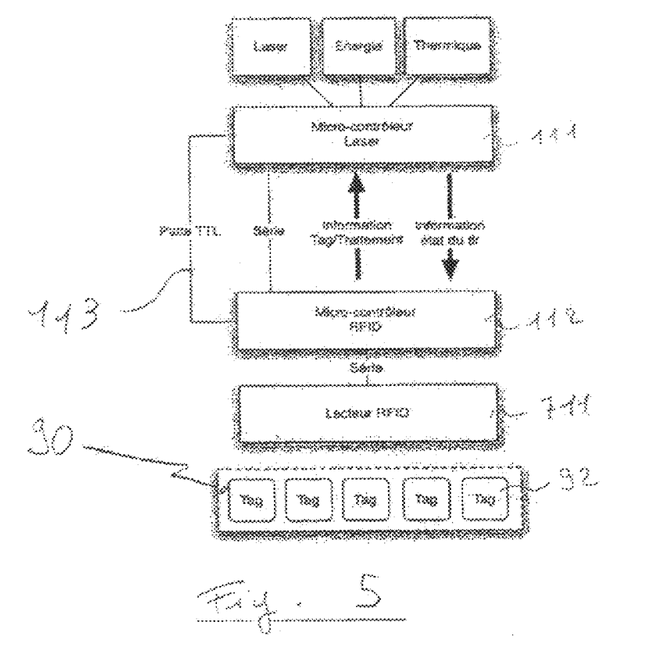
FIG. 5 is a diagram of communication between the RFID tag and the handpiece.

FIG. 5 shows a communications procedure between the RFID tag and the handpiece as follows:

The handpiece contains two microcontrollers (111 and 112). Microcontroller 111 manages the laser, the energy, heat regulation and the MMI; microcontroller 112 manages the adhesive supports 90. Management of firing is shared by the two microcontrollers 111 and 112. Firing can be stopped by microcontroller 111, because of too high a temperature or following an emergency stop request. Restarting treatment is limited by these stopping conditions.

Figure 6A:
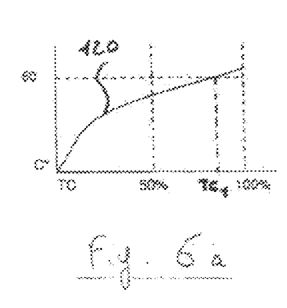
FIGS. 6a, 6b and 6c, show temperature curves against heating time of the system.
Figure 6B:
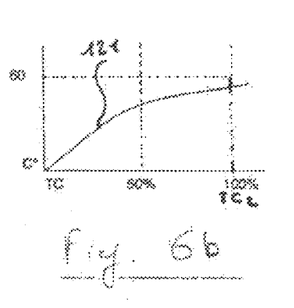
Figure 6C:
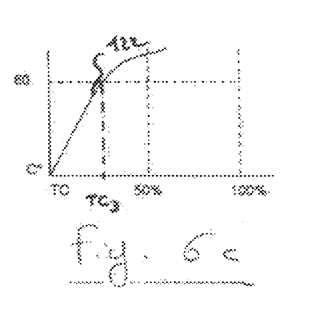

With reference to FIGS. 6a, 6b and 6c, a pyrometer in the handpiece, managed by the microcontroller (111), stops the laser firing if the skin temperature is higher than a critical temperature, e.g. 60° C. These figures are graphs showing temperature curves (120, 121 and 122) (degrees Celsius as the ordinate against heating time (TC) as abscissa); TC1, TC2 and TC3 represent the times at which firing is stopped. If firing has been stopped by the pyrometer, it can again be authorized once after a safety period (e.g. 5 seconds) if, during the first firing, the firing time was less or equal to half of the preset firing duration (managed by the microcontroller (112)). This is the case in FIG. 6c. Thus the figures show the following situations:

FIG. 6a shows the case of firing being stopped (TC1—heating time 1) after 50% of the preset firing duration has elapsed. In this case firing cannot be resumed.

FIG. 6b shows the case of firing not being stopped before the end of the preset firing duration (TC2—heating time 2), and FIG. 6c shows the case of firing being stopped (TC3—heating time 3) before 50% of the preset firing duration has elapsed; in this case firing can be resumed.

If the pyrometer trips after 50% (FIG. 6a) of the normal firing duration has elapsed, a beep should indicate the end of normal firing; this is managed by the microcontroller (111). If the pyrometer is triggered before 50% has elapsed, a Man-Machine Interface (MMI) display shows the user that he can resume firing.

If the user stops firing (a voluntary or involuntary stop caused by the user) and the time of stopping is not more than 75% of the preset firing duration, resumption of firing can be authorized once after 5 seconds, and is valid for 60 minutes.

If the emergency stop is activated, there may be a verification procedure which would have to be followed by the user.

The presence of an RFID tag (92), detected by the handpiece RFID reader, is indicated by the TTL pin (113) of the microcontroller (112). The presence of an RFID tag (92) gives no information concerning its status. To find out the status of the RFID tag (92), a "read settings" message must be sent to microcontroller 112. This command produces information on the treatment status of the RFID tag (92) in the range of the RFID reader (711). The various statuses of an RFID tag (92) are:

Treated;
OK (not treated);
Immediate resumption (identical to not treated); and
Waiting before resuming (5 seconds).

Microcontroller 111 recognizes five messages from microcontroller 112:

INIT: Initialization of the clock and of the handpiece identifier;

PARAM: Retrieve information on status of the RFID tag 92, firing power and duration, the device only being able to fire if the PARAM status is OK;

START: Start of firing;
STOP: End of firing; and
PAUSE: Premature stopping of firing.

On starting up the handpiece, the microcontroller (111) initializes the clock of microcontroller 112 with the message INIT. The two clocks are synchronized. At the rising edge of the TTL pin (113) of microcontroller 112, microcontroller 111 requests the firing parameters with the message PARAM. Depending on the response from microcontroller 112, the MMI is updated and firing is authorized. During firing, microcontroller 111 indicates the progress of firing to microcontroller 112 with the messages START, STOP and PAUSE. Microcontroller 112 updates the RFID tag (92) information according to these messages. The handpiece clock is controlled by one or other of microcontrollers 111 or 112, chosen indifferently by those skilled in the art. The clock does not contain the exact date and time, but date information related to handpiece start-up. It has a chronometer function and can be reinitialized following a prolonged interruption of the supply to the battery. In this case, if an RFID tag (92) has been treated, its treatment start date is later than the current date. Even if treatment has not been completed, the RFID tag (92) is considered as treated.

Figure 7:
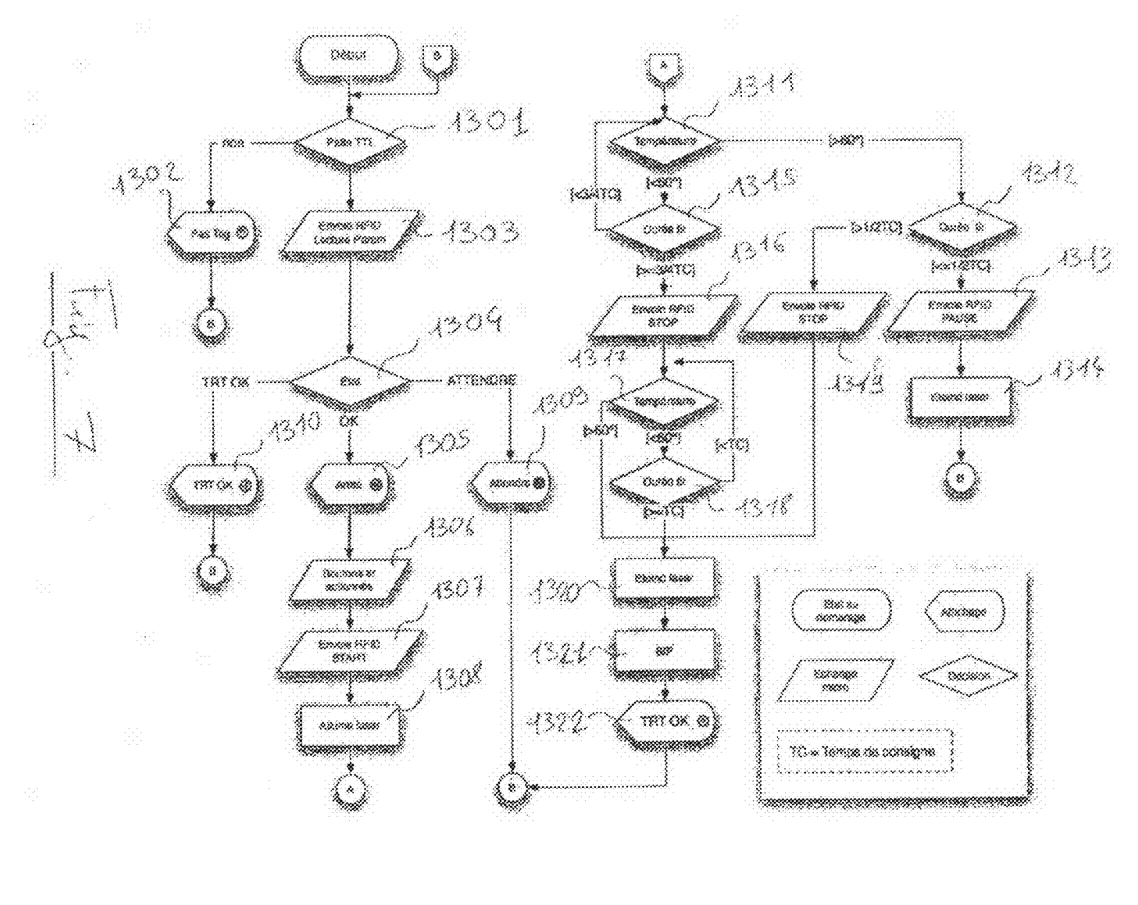
FIG. 7 is a flow-chart of how the system functions.

FIG. 7 represents a firing authorization management algorithm for microcontroller 111 and a firing authorization management algorithm for microcontroller 112. Both have been previously set out. Initially either an RFID tag is detected (1301) or it is not detected (1302). If an RFID tag is detected (1301), reading its parameters is initiated (1303) to determine the status of the RFID tag (1304). If the status is "OK" then via the MMI the handpiece indicates that it is "loaded" (1305) and, if firing is activated (1306), microcontroller 111 sends microcontroller 112 the "START" message (1307) indicating the start of firing. Finally the laser is switched on (1308). If the message is "WAIT", then the handpiece indicates that it is "waiting" (1309) and returns to the start. If the message is "TRT OK" (treated) then the handpiece indicates that the area has been treated (1310) and returns to the start.

If firing has been initiated (box A), the temperature is measured (1311). If this temperature is above 60°, then the time is also measured (1312). If this time is less than 50% of the preset firing time, a "PAUSE" message (1313) is sent to microcontroller 112, and the laser is switched off (1314).

If the temperature measured (1311) is below 60°, then the time is also measured (1315). If this time is less than 75% of the preset firing time, the temperature is again measured (1311). If, on the other hand, the time is more than 75% of the preset TC firing time, a "STOP" message (1316) is sent to microcontroller 112. The temperature is then measured (1317). If the temperature is lower than 60°, the length of time of firing is verified (1318); if the duration of firing is less than the preset TC firing time (indicating that firing has not yet finished), then the temperature is checked again (1317). This loop (1317 and 1318) continues until the temperature exceeds 60° or until the length of firing reaches or exceeds the heating time TC. In both cases, the laser is switched off (1320), a beep sounds (1321), or any other means of indication is triggered using the MMI, to inform the user of the end of treatment of this area and an 'end of treatment' message is displayed (1322). The time is again measured (1312); if the firing time is more than 50% of the heating time (TC), then a "STOP" message is sent to the microcontroller (1319), and the laser is switched off (1320). If the firing time is less than or equal to 50% of the heating time a "PAUSE" message is sent to the microcontroller (1314) and the laser is switched off.

Figure 8:
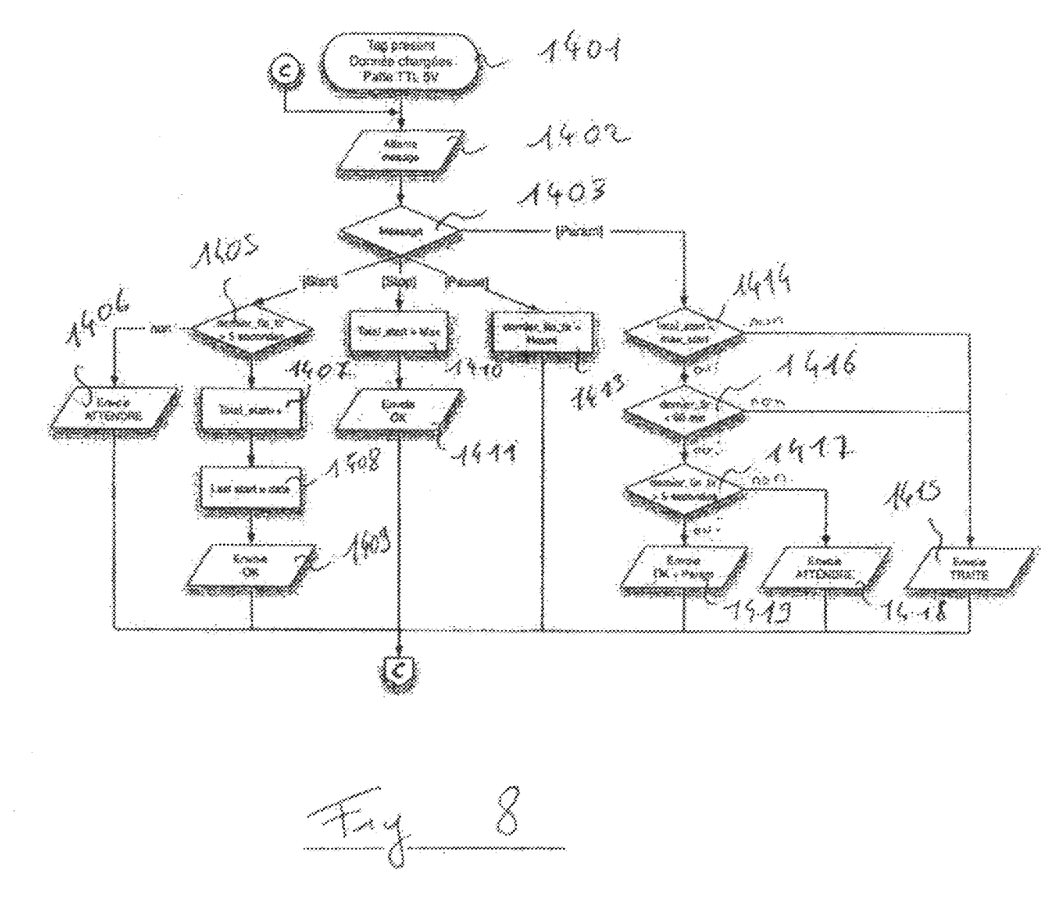
FIG. 8 is a flow-chart for management of the authorization to fire.

With reference to FIG. 8, we will describe a firing authorization management algorithm for microcontroller 111. If an RFID tag is detected (1401), microcontroller 111 waits for a message (1402) from microcontroller 112. When a message (1403) is received, it is analyzed. If the message is "START", and the last firing was less than 5 seconds previously (1405), the microcontroller (111) sends the message "WAIT" (1406). If, on the other hand, the last firing was more than 5 seconds before, a Total_Start variable (indicating the number of firings performed) is increased by one unit (1407) and a Last_Start variable (indicating the date of the last firing) is updated (1408). Finally an "OK" message is sent (1409).

If the message received is "STOP", then the Total_Start variable is set at a predetermined maximum (1410) and the "OK" message is sent (1411).

If the message received is "PAUSE", the date of the end of firing is recorded (1413).

Finally, if the message received is "PARAM", the Total_Start variable (1414) is analyzed. If this variable is lower than the predefined maximum, then the message "TREATED" is sent (1415). If this is not the case, the Last_Start variable (1416) is analyzed and if this variable is greater than 60 minutes, then the message "TREATED" is sent (1415). If this is not the case, it is verified whether the last firing occurred more than 5 seconds previously (1417); if this is not the case, the message "WAIT" is sent (1418). If, on the other hand, the last firing did occur more than 5 seconds previously, the message "OK" is sent and the parameters are read (1419). The information contained in the RFID tag can be selected from the following: unique RFID tag identifier, date of manufacture, date of expiry, handpiece settings identification depending on skin type, manufacturing batch number of the adhesive support (90).

All the figures (percentages, temperature, etc.) in the description are given purely as an indication to guide implementation of the invention. Those skilled in the art may use other figures determined for example by experimentation without leaving the context of the invention.

The invention claimed is:

1. A system for dermatological treatment comprising:
   an energy source suitable for a biochemical activation of healing; and
   at least one means of interaction between the energy source and a patient,
   wherein the means of interaction consists essentially of a continuous adhesive support suitable for placement close to an area to be treated, the support having at least one means of identification interacting without contact with a sensor allowing the energy source to function only when a distance between the sensor and the means of identification is below a threshold value.

2. The system for dermatological treatment according to claim 1, wherein the adhesive support contains at least 2 means of identification spaced apart at a distance at least equal to a whole multiple of a width of the area treated by an individual shot.

3. The system for dermatological treatment according to claim 2, wherein the means of identification are spaced at a distance equal to the width of the area treated by an individual shot.

4. The system for dermatological treatment according to claim 1, wherein the means of identification interacts with the energy source through a contact.

5. The system for dermatological treatment according to claim 1, wherein parameters for the energy source to function are memorized in the means of identification and communicated to a device controlling the energy source.

6. The system for dermatological treatment according to claim 1, wherein there is information characterizing the state of the area to be treated, near which there is an adhesive support having a means of identification, the information being recorded in the means of identification, and relating to one of the following states:
   the area to be treated has not been treated;
   the area to be treated is being treated; and
   treatment of the area to be treated has been completed.

7. The system for dermatological treatment according to claim 6, wherein a control device receiving the information about the state of the area to be treated includes a means of preventing a second use of the adhesive support containing a means of identification when this has already been used once for treatment of the area to be treated.

8. The system for dermatological treatment according to claim 1 further comprising a wound closure device adapted to be inserted in edges of a wound, an absorption coefficient of which for the energy source being considered is less than that of the skin.

9. The system for dermatological treatment according to claim 1 further comprising a handpiece incorporating a source of electromagnetic radiation for biochemical activation of healing and a means of interaction with the adhesive support.

10. The system for dermatological treatment according to claim 1 further comprising a handpiece incorporating a laser source and a means of interaction with the said adhesive support.

11. The system for dermatological treatment according to claim 1 further comprising the energy source controlled by a microprocessor receiving a signal from the sensor able to interact with the means of identification of a dressing or the adhesive support.

12. The system for dermatological treatment according to claim 9, wherein the handpiece includes a radiofrequency reader.

13. The system for dermatological treatment according to claim 12, wherein a range of a radiofrequency antenna in the radiofrequency reader is less than 5 mm.

14. An adhesive support for a system for dermatological treatment according to claim 1, wherein the means of identification, further comprises means of preventing second use of the adhesive support if the latter has already been used for the treatment of the area to be treated.

15. The adhesive support according to claim 14 further comprising, on its upper surface, markings spaced apart by a length equal to the width of the area treated by an individual shot.

16. The adhesive support according to claim 14, wherein the adhesive support is opaque.

17. The adhesive support according to claim 14 further comprising a transponder.

18. The adhesive support according to claim 17, wherein the transponder functions in a frequency band between 13 and 14 MHz.

19. A method of dermatological treatment suitable for the biochemical activation of healing in a patient, the method comprising:
   (i) positioning, near the area to be treated, an adhesive support as defined in claim 17, which has a means of identification which interacts without contact with a sensor controlling the functioning of an energy source, and
   (ii) positioning the energy source, including a sensor controlling its functioning at a distance between the sensor and the means of identification of less than a threshold value so that the said source of energy is activated allowing the biochemical activation of healing in the area under treatment.

20. The method of dermatological treatment according to claim 19, wherein the method is suitable for wound closure.

21. The method of dermatological treatment according to claim 20 further comprising a preliminary step where a wound closure device is inserted into edges of the wound, this device having an absorption coefficient for the energy source being considered lower than that of the skin.

* * * * *